United States Patent [19]

Dunn

[11] 4,305,404

[45] Dec. 15, 1981

[54] URINE METER

[75] Inventor: William J. Dunn, Libertyville, Ill.

[73] Assignee: The Kendall Company, Boston, Mass.

[21] Appl. No.: 139,322

[22] Filed: Apr. 11, 1980

[51] Int. Cl.$^3$ ............................................. A61B 19/00
[52] U.S. Cl. ..................................... 128/762; 73/219; 73/427; 128/767; 128/768; 128/771
[58] Field of Search ............. 128/762, 767, 768, 771, 128/295; 73/219, 426, 429, 427

[56] References Cited

U.S. PATENT DOCUMENTS

| | | | |
|---|---|---|---|
| 3,374,939 | 3/1968 | McMenimen | 128/295 X |
| 3,601,119 | 8/1971 | Engelsher | 128/768 X |
| 3,683,894 | 8/1972 | Villari | 128/771 X |
| 3,776,231 | 12/1973 | Holbrook et al. | 128/771 X |
| 3,831,446 | 8/1974 | Dye | 128/771 X |
| 3,906,935 | 9/1975 | Raia | 128/768 X |
| 4,095,589 | 6/1978 | Manschot et al. | 128/771 X |

FOREIGN PATENT DOCUMENTS

| | | | |
|---|---|---|---|
| 1007533 | 3/1977 | Canada | 128/771 |
| 2289165 | 5/1976 | France | 128/771 |

*Primary Examiner*—Kyle L. Howell
*Attorney, Agent, or Firm*—Powell L. Sprunger

[57] ABSTRACT

A urine meter comprising, a container having a cavity for collection of urine, and a drainage tube for draining urine from a patient. The meter has a receptacle having a chamber, with the drainage tube defining a port communicating with an upper portion of the receptacle for passage of urine into the chamber. The receptacle has a baffle extending across an upper portion of the receptacle below the drainage tube port and defining opening means permitting passage of urine from the drainage tube port into the chamber. The meter communicates between an upper portion of the receptacle and an upper portion of the container to permit passage of urine from the chamber to the cavity by tilting the receptacle while the baffle prevents passage of urine into the drainage tube.

15 Claims, 5 Drawing Figures

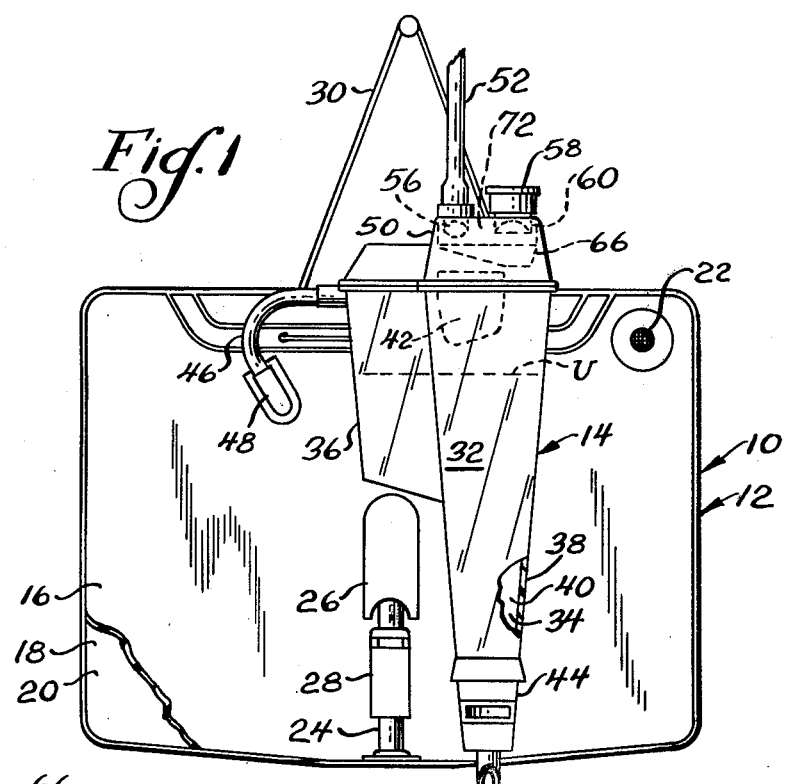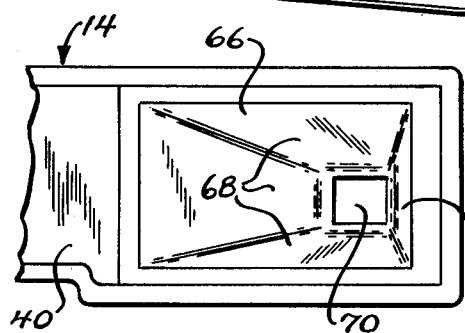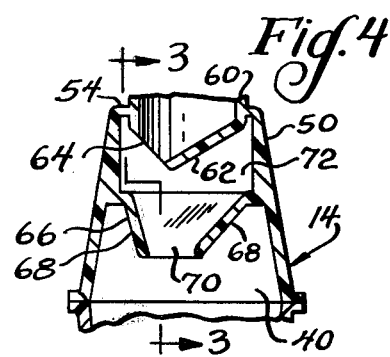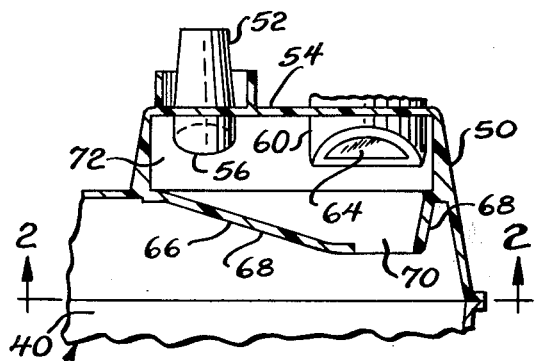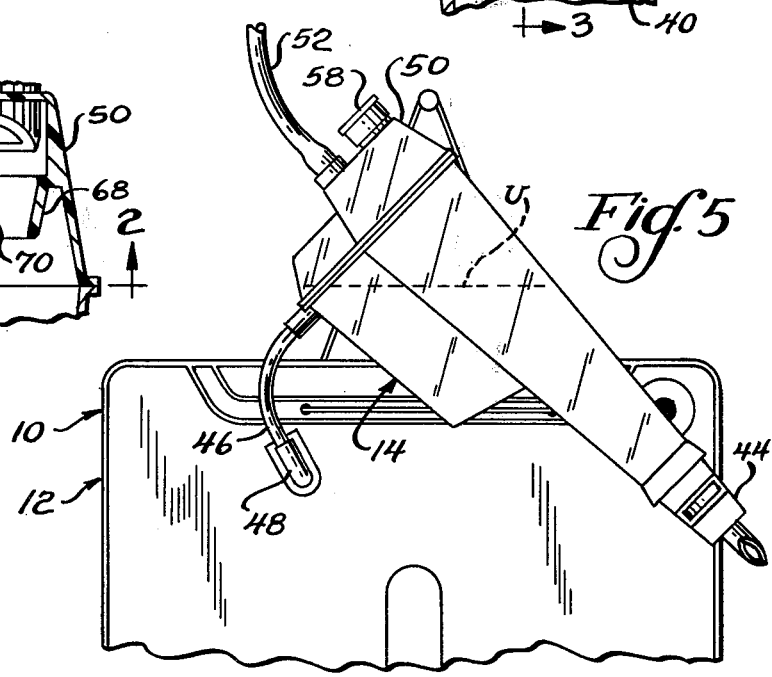

URINE METER

BACKGROUND OF THE INVENTION

The present invention relates to urine receptacles, and more particularly to urine meters.

Before the present invention, urine meters have been proposed of the type having a container, a receptacle, and a drainage tube communicating with an upper portion of the receptacle. The receptacle may be used to determine incoming urine volumes with relative accuracy, and the receptacle may be periodically emptied into the container where the urine is stored. However, it is necessary to prevent reflux of urine into the drainage tube when the receptacle is emptied, since the refluxing urine increases the chance of retrograde bacteria movement into the drainage tube and possibly the patient. Also, it is desirable to prevent reflux of urine against a vent on the receptacle, since continued contact of urine against the vent may cause blockage of the vent.

SUMMARY OF THE INVENTION

A principal feature of the present invention is the provision of an improved urine meter for receiving urine from a patient.

The urine meter comprises, a container having a cavity for collection of urine, and a drainage tube for draining urine from a patient. The meter has a receptacle having a chamber and a baffle extending across an upper portion of the receptacle toward one side of the receptacle and defining a compartment above the chamber. The baffle defines a lower opening communicating between the compartment and chamber, and the drainage tube has a down stream end in the compartment defining a drip tube, with the receptacle having a vent communicating with the compartment. The urine meter has means communicating between an upper portion of the receptacle adjacent the other side of the receptacle and an upper portion of the container to permit passage of urine from the chamber to the cavity by tilting the receptacle.

A feature of the present invention is that the baffle prevents passage of urine into the drip tube when the receptacle is tilted to pass urine from the receptacle into the container.

Another feature of the invention is that the baffle prevents passage of urine against the vent when the receptacle is placed in the tilted configuration.

Further features will become more fully apparent in the following description of the embodiments of this invention and from the appended claims.

DESCRIPTION OF THE DRAWINGS

In the drawings:

FIG. 1 is a fragmentary front plan view of a urine meter of the present invention;

FIG. 2 is a lower plan view of a baffle in a receptacle of the urine meter taken substantially as indicated along the line 2—2 of FIG. 3.

FIG. 3 is a fragmentary sectional view taken substantially as indicated along the line 3—3 of FIG. 4;

FIG. 4 is a fragmentary sectional view of a lower portion of a vent and the baffle in the receptacle; and FIG. 5 is a fragmentary front plan view of the urine meter showing the receptacle being tilted to pass urine into a container of the urine meter.

DESCRIPTION OF THE PREFERRED EMBODIMENTS

Referring now to FIG. 1, there is shown a urine meter generally designated 10 having a container 12 and a receptacle 14. The container 12 has a front wall 16 and a rear wall 18 of flexible material, such as a suitable plastic, being joined together around the periphery thereof and defining a cavity 20 between the front and rear walls 16 and 18. The front wall 16 of the container 12 has a vent 22 with a bacteria filter of known type communicating with the container cavity 20. The container 12 has a tubular section 24 communicating with a lower portion of the cavity 20, and having an outer end removably received in a pocket 26, with the tubular section 24 having a releasable clamp 28 on the tubular section. Thus, when it is desirable to drain urine from the container 12, the tubular section 24 is removed from the pocket 26, and the clamp 28 is released to permit passage of urine through the tubular section 24. The container 12 also has a string 30 attached to an upper portion of the container 12 to permit hanging of the urine meter 10 from a suitable object during use.

With reference to FIGS. 1-4, the receptacle 14 has a front wall 32, a rear wall 34, and a pair of side walls 36 and 38 defining a chamber 40 in the receptacle 14. The receptacle 14 has a hook 42 extending from the rear wall 34 and spaced from the rear wall 34 to receive an upper portion of the container 12 in order to support the receptacle 14 on the upper portion of the container 12. The receptacle 14 has a lower valve 44 to permit draining of urine when desired from the receptacle chamber 40 to obtain a specimen of urine. The urine meter 10 has a flexible tube 46 having one end connected to the receptacle 14 adjacent the side wall 36 such that it communicates with an upper portion of the chamber 40, and the other end of the tube 46 is attached by a connector 48 to an upper portion of the container 12 on the front wall 16, such that the tube 46 communicates with an upper portion of the cavity 20. Thus, the tube 46 communicates between an upper portion of the chamber 40 and an upper portion of the cavity 20 for a purpose which will be described below.

As shown, the receptacle 14 has a raised portion 50 adjacent an upper end of the receptacle 14. The urine meter 10 has a drainage tube 52 for draining urine from the patient, with a downstream end of the drainage tube 52 extending through an upper wall 54 of the raised portion 50 into the receptacle 14 to define a drip tube 56 inside the receptacle 14. The receptacle 14 has a vent 58 attached to the upper wall 54, with the vent 58 having a tubular extension 60 depending inside the receptacle 14. The tubular extension 60 has a generally closed bottom 62, and an opening 64 at one side communicating with the vent 58 which has a bacteria filter element of known type. Thus, the vent 58 permits passage of filtered air from the atmosphere through the tubular extension 60 and opening 64 into the inside of the receptacle 14.

As shown, the receptacle 14 has a baffle 66 extending across the lower part of the raised portion 50, with the baffle 66 having downwardly sloping walls 68 defining a lower opening 70 adjacent the side wall 38. The baffle 66 defines a compartment 72 in the raised portion 50, with the drip tube 56 being located in the compartment 72 above the walls 68 of the baffle 66, and with the tubular extension 60 of the vent 58 being located in the compartment 72 above the baffle opening 70.

In use, urine drains from a catheter (not shown) in the patient through the drainage tube 52 and drip tube 56 into the compartment 72, where it drains along the wall 68 of the baffle 66 through the opening 70 into the receptacle chamber 40. As the urine collects in the chamber 40 of the receptacle 14, the volume of urine may be determined by suitable indicia (not shown) on the front wall 32 of the receptacle 14. When a suitable volume of urine U has been collected in the receptacle chamber 40, as shown in FIG. 1, the urine U may be emptied into the container 12 for retention therein. In order to accomplish this result, the receptacle 14 is lifted from the container 12 to remove the hook 42 from the upper portion of the container 12, and the receptacle 14 is then tilted, as shown in FIG. 5, such that the urine U passes through the tube 46 and the connector 48 into the cavity 20 of the container 12. In this manner, the urine U is transferred from the receptacle 14 to the container 12 in order to initiate collection of a new volume of urine in the receptacle 14. Also, the urine U may be permitted to overflow from the receptacle 14 through the tube 46 into the container 12 during collection of urine. When the receptacle 14 is tilted to pass urine into the container 12, the baffle 66 prevents passage of urine into the drip tube 56 in the event that the receptacle 14 is tilted too far during the emptying procedure. Thus, the present invention eliminates the possibility that urine may reflux into the drip tube 56 and drainage tube 52 in order to minimize the possibility of retrograde bacteria movement into the drainage tube 52 and possibly the patient. Also, the baffle 66 prevents passage of urine into the vent 58 during the emptying procedure in order to prevent closure of the vent 58 which may otherwise be caused by prolonged contact of urine against the filter element of the vent 58. The tubular extension 60 also prevents contact of urine against the vent 58 in the event that urine should splash through the baffle opening 70 when the receptacle 14 is in an upright or tilted configuration.

The foregoing detailed description is given for clearness of understanding only, and no unnecessary limitations should be understood therefrom, as modifications will be obvious to those skilled in the art.

I claim:

1. A urine meter, comprising:
a container having a cavity for collection of urine;
a drainage tube for draining urine from a patient;
a receptacle having a chamber, with the drainage tube defining a port communicating with an upper portion of the receptacle for passage of urine into the chamber, said receptacle having a baffle extending across an upper portion of the receptacle below the drainage tube port and defining opening means permitting passage of urine from the drainage tube port into the chamber, said receptacle having an upper raised portion to receive the drainage tube and in which the baffle extends across a lower portion of the raised portion; and
means communicating between an upper portion of the receptacle and an upper portion of the container to permit passage of urine from the chamber to the cavity by tilting the receptacle while said baffle prevents passage of urine into the drainage tube.

2. The meter of claim 1 including means for releasably supporting the receptacle on a front side of the container.

3. The meter of claim 2 wherein the supporting means comprises a hook extending from a rear portion of the receptacle for placement over an upper portion of the container.

4. The meter of claim 1 wherein the communicating means comprises a tube extending between an upper portion of the receptacle and an upper portion of the container.

5. The meter of claim 1 wherein the communicating means communicates with one side of the receptacle, and in which the baffle extends toward the other side of the receptacle.

6. The meter of claim 5 wherein the baffle defines an opening adjacent the other side of the receptacle.

7. The meter of claim 1 wherein the receptacle includes a vent located above the baffle.

8. The meter of claim 7 wherein the vent includes a depending tubular extension having a closed bottom and defining an opening at one side of the tubular extension.

9. The meter of claim 1 wherein the baffle has a plurality of downwardly sloping walls defining a lower opening.

10. The meter of claim 1 wherein the container has a pair of opposed flexible walls defining the cavity.

11. A urine meter, comprising:
a container having a cavity for collection of urine;
a drainage tube for draining urine from a patient;
a receptacle having a chamber and a baffle extending across an upper portion of the receptacle toward one side of the receptacle and defining a compartment above the chamber, with the baffle defining a lower opening communicating between the compartment and chamber, with said drainage tube having a downstream end in said compartment defining a drip tube, and with said receptacle having a vent having a bacteria filter element, said vent being located above the baffle and communicating with said compartment; and
means communicating between an upper portion of the receptacle adjacent the other side of the receptacle and an upper portion of the container to permit passage of urine from the chamber to the cavity by tilting the receptacle while the baffle prevents passage of urine into the drip tube and vent.

12. The meter of claim 11 wherein the baffle opening is located adjacent the one side of the receptacle.

13. The meter of claim 11 wherein the vent is located above the baffle opening.

14. The meter of claim 11 wherein the vent has a depending tubular extension in said compartment having a closed bottom and an opening at one side.

15. A urine meter, comprising:
a container having a cavity for collection of urine;
a drainage tube for draining urine from a patient;
a receptacle having a chamber, with the drainage tube defining a port communicating with an upper portion of the receptacle for passage of urine into the chamber, said receptacle having a baffle extending across an upper portion of the receptacle below the drainage tube port and defining opening means permitting passage of urine from the drainage tube port into the chamber, said receptacle having a vent located above the baffle, the vent including a depending tubular extension having a closed bottom and defining an opening at one side of the tubular extension; and
means communicating between an upper portion of the receptacle and an upper portion of the container to permit passage of urine from the chamber to the cavity by tilting the receptacle while said baffle prevents passage of urine into the drainage tube.

* * * * *